(12) United States Patent
Walling et al.

(10) Patent No.: US 8,821,056 B2
(45) Date of Patent: Sep. 2, 2014

(54) ANTIPERSPIRANT COMPOSITIONS AND METHODS FOR MAKING SAME

(75) Inventors: David William Walling, Cincinnati, OH (US); Eric Shane Henley, West Harrison, IN (US)

(73) Assignee: The Procter & Gamble Company, Cincinnati, OH (US)

( * ) Notice: Subject to any disclaimer, the term of this patent is extended or adjusted under 35 U.S.C. 154(b) by 96 days.

(21) Appl. No.: 13/456,508

(22) Filed: Apr. 26, 2012

(65) Prior Publication Data

US 2012/0205002 A1 Aug. 16, 2012

Related U.S. Application Data

(62) Division of application No. 11/518,104, filed on Sep. 8, 2006, now Pat. No. 8,187,578.

(51) Int. Cl.
*B43K 5/06* (2006.01)

(52) U.S. Cl.
USPC ............... 401/175; 401/75; 220/665; 424/65

(58) Field of Classification Search
USPC ............... 401/78, 82, 171, 172, 174, 175, 75; 424/65–68; 220/665, 662, 87.1; 206/229, 223, 38, 216
See application file for complete search history.

(56) References Cited

U.S. PATENT DOCUMENTS

| | | |
|---|---|---|
| 1,969,331 A | 8/1934 | Small |
| 2,022,075 A | 11/1935 | Carbrera |
| 2,352,075 A | 6/1944 | Brownstein |
| 2,626,847 A | 1/1953 | Brown |
| 3,205,764 A | 9/1965 | Letter |
| 3,792,068 A | 2/1974 | Luedders et al. |
| 3,837,574 A | 9/1974 | Curran |
| 3,887,692 A | 6/1975 | Gilman |
| 3,904,741 A | 9/1975 | Jones et al. |
| 3,912,079 A | 10/1975 | Selchow |
| 4,120,948 A | 10/1978 | Shelton |
| 4,139,311 A | 2/1979 | Lorscheidt |
| 4,359,456 A | 11/1982 | Gosling et al. |
| 4,363,560 A | 12/1982 | Gentile |
| 4,621,935 A | 11/1986 | Sussman |
| 4,985,238 A | 1/1991 | Tanner et al. |
| 5,240,337 A | 8/1993 | Gruner |
| 5,286,126 A | 2/1994 | Harris et al. |
| 5,346,323 A | 9/1994 | Harris et al. |

(Continued)

FOREIGN PATENT DOCUMENTS

| | | |
|---|---|---|
| EP | 310488 | 4/1989 |
| EP | 1072214 | 1/2001 |

(Continued)

OTHER PUBLICATIONS

U.S. Appl. No. 14/205,872, Mar. 13, 2014 Sturgis.*

(Continued)

*Primary Examiner* — David Walczak

(57) ABSTRACT

A consumer product comprising packaging including a product chamber and an outer jacket at least partially surrounding the product chamber; and an antiperspirant composition disposed within the product chamber, wherein the composition exhibits an average standard deviation of less than or equal to about 5 of penetration peak force measurements taken in accordance with a penetration test method as defined herein.

12 Claims, 3 Drawing Sheets

(56) References Cited

U.S. PATENT DOCUMENTS

| | | |
|---|---|---|
| 5,538,161 A | 7/1996 | Koehler |
| 5,609,855 A | 3/1997 | Oh et al. |
| 5,833,382 A | 11/1998 | Jenks et al. |
| 5,902,062 A | 5/1999 | Rosenblatt et al. |
| 5,972,319 A | 10/1999 | Linn et al. |
| 5,976,514 A | 11/1999 | Guskey et al. |
| 6,001,377 A | 12/1999 | SaNogueira, Jr. et al. |
| 6,013,248 A | 1/2000 | Luebbe et al. |
| 6,013,270 A | 1/2000 | Hargraves et al. |
| 6,013,271 A | 1/2000 | Doughty et al. |
| 6,024,942 A | 2/2000 | Tanner et al. |
| 6,048,518 A | 4/2000 | Bianchi et al. |
| 6,171,601 B1 | 1/2001 | Gardlik et al. |
| 6,231,841 B1 | 5/2001 | Franklin et al. |
| 6,258,346 B1 | 7/2001 | Scavone et al. |
| 6,338,840 B1 | 1/2002 | Allan et al. |
| 6,338,841 B1 | 1/2002 | Mattai et al. |
| D454,229 S | 3/2002 | Look |
| 6,352,688 B1 | 3/2002 | Scavone et al. |
| 6,391,291 B1 * | 5/2002 | Clare et al. ............ 424/65 |
| 6,503,522 B2 * | 1/2003 | Lawson et al. .......... 424/401 |
| 6,592,278 B1 | 7/2003 | Holthaus |
| 6,663,854 B1 | 12/2003 | Shen et al. |
| 6,703,005 B2 | 3/2004 | Allan et al. |
| 6,776,981 B2 | 8/2004 | Elliott et al. |
| 6,835,373 B2 | 12/2004 | Kolodzik et al. |
| 6,852,193 B2 | 2/2005 | Kneafsey et al. |
| 7,229,611 B2 | 6/2007 | Zamudo-Tena et al. |
| 7,389,894 B2 | 6/2008 | Danne et al. |
| 7,452,526 B2 | 11/2008 | Walling et al. |
| 2003/0108376 A1 | 6/2003 | Hurlburt |
| 2007/0092541 A1 | 4/2007 | Walling et al. |
| 2007/0114142 A1 | 5/2007 | Sine et al. |
| 2008/0063616 A1 | 3/2008 | Walling et al. |

FOREIGN PATENT DOCUMENTS

| | | |
|---|---|---|
| FR | 2567376 | 1/1986 |
| FR | 2639260 | 5/1990 |
| GB | 1 347 950 | 2/1974 |
| GB | 2 048 229 | 12/1980 |
| GB | 2 144 992 | 3/1985 |
| WO | WO 01/87252 A2 | 11/2001 |
| WO | WO 2005/084629 A1 | 9/2005 |

OTHER PUBLICATIONS

U.S. Appl. No. 14/205,924, Mar. 12, 2014 Sturgis.*
U.S. Appl. No. 14/206,067, Mar. 12, 2014 Sturgis.*
U.S. Appl. No. 14/206,134, Mar. 12, 2014 Sturgis.*
International Search Report for PCT/IB2007/053615 dated Feb. 18, 2004.
International Search Report PCT/IB2007/053615 including the Written Opinion of the International Searching Authority mailed May 9, 2008, 19 pages.

* cited by examiner

ANTIPERSPIRANT COMPOSITIONS AND METHODS FOR MAKING SAME

CROSS REFERENCE TO RELATED APPLICATION

This reference is a divisional application of U.S. application Ser. No. 11/518,104, filed on Sep. 8, 2006, now U.S. Pat. No. 8,187,578, which is incorporated herein by reference.

FIELD OF THE INVENTION

The present invention is directed to antiperspirant and deodorant products and methods for making such products.

BACKGROUND OF THE INVENTION

There are many types of solid deodorant and antiperspirant sticks that are commercially available or otherwise known in the art. These solid sticks are designed to provide effective perspiration and odor control while also being cosmetically acceptable during and after application onto the underarm area of the skin, and are typically packaged in dispensing containers suitable for conventional application of the composition to the skin by a consumer.

Solid deodorants and antiperspirants are typically manufactured and filled into dispensing containers prior to complete curing or solidification. The uniformity of properties of the post-cured deodorants and antiperspirants can be negatively affected however by containers that do not permit efficient heat transfer. Actives or other cosmetic materials may settle during curing for example, or crystal formation may be affected such that the "feel" of the product varies over multiple uses. Containers that provide efficient heat transfer though may be limited in design and material make-up. Thus packaging, marketing, and merchandising related innovation can be severely compromised in an effort to produce uniform deodorants and antiperspirants.

SUMMARY OF THE INVENTION

The present invention is directed to consumer care products, and in particular, antiperspirant and deodorant products. In accordance with one of the preferred embodiments, there has now been provided a consumer product comprising packaging comprising a product chamber and an outer jacket at least partially surrounding the product chamber; and an antiperspirant composition disposed within the product chamber. The antiperspirant composition exhibits an average standard deviation of less than or equal to about 5 of penetration peak force measurements taken in accordance with a penetration test method as defined herein. In accordance with another preferred embodiment, the antiperspirant composition exhibits an average standard deviation of less than or equal to about 40 of Hardness Modulus measurements taken in accordance with a penetration test method as defined herein.

The present invention is also directed to processes for making antiperspirant and deodorant products. In accordance with one of the preferred embodiments, there has now been provided a process comprising the steps of: (a) providing a container; (b) providing a material process stream comprising a gellant and heating the material process stream to a first temperature to substantially completely melt the gellant; (c) lowering the material process stream to a second temperature that is lower than the first temperature by at least 10° C., but is still above the onset of crystallization of the gellant; (d) after and/or during step (c), adding an antiperspirant and/or deodorant active to the material process stream to form an antiperspirant composition; (d) charging a volume of the antiperspirant composition into the container; (f) disposing an outer jacket at least partially around the container to define a double-walled container; and (g) achieving an antiperspirant composition temperature that is lower than the second temperature by 15° C. within 30 minutes of completing steps (e) and (f).

In accordance with another preferred process embodiment, there has now been provided a process comprising the steps of: (a) providing a double-walled container comprising a product chamber and an outer jacket that at least partially surrounds the product chamber; (b) forming a hot material process stream comprising a solvent and a gellant dissolved therein, the hot process material stream having a first temperature; (c) forming a cold process stream comprising an antiperspirant and/or deodorant active and having a second temperature, wherein the second temperature is at least 20° C. below the first temperature; (d) combining the hot material process stream and the one cold material process stream together in a mixing chamber to form a mixed process stream; and (e) charging a volume of the mixed process stream into the product chamber.

BRIEF DESCRIPTION OF THE DRAWINGS

While the specification concludes with claims particularly pointing out and distinctly claiming the subject matter which is regarded as forming the present invention, it is believed that illustrative embodiments of the present invention may be better understood from the following description taken in conjunction with the accompanying drawings, in which:

DETAILED DESCRIPTION OF THE INVENTION

Figure 1:
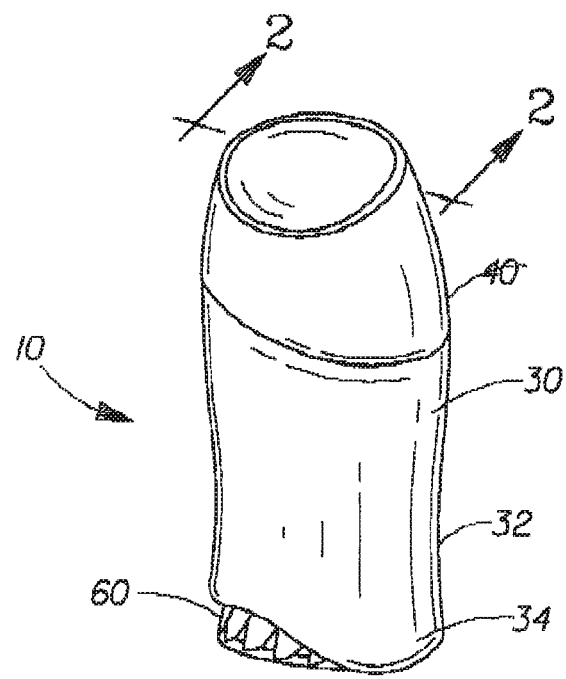
FIG. 1 is a perspective view of an exemplary package in accordance with the present invention.

It is to be understood that the scope of the claims is not limited to the specific articles, devices, methods, conditions or parameters described and/or shown herein, and that the terminology used herein is for the purpose of describing particular embodiments by way of example only and is not intended to be limiting of the claimed invention. Also, as used in the specification, including the appended claims, the singular forms "a," "an," and "the" include the plural, and reference to a particular numerical value includes at least that particular value, unless the context clearly dictates otherwise. When a range of values is expressed, another embodiment includes from the one particular value and/or to the other particular value. Similarly, when values are expressed as approximations, by use of the antecedent basis "about," it will be understood that the particular values forms another embodiment. All ranges are inclusive and combinable.

While the specification concludes with the claims particularly pointing and distinctly claiming the invention, it is believed that the present invention will be better understood from the following description.

"Antiperspirants", as used herein, includes antiperspirants, deodorants, deodorant/antiperspirants and body sprays, and may also be considered as beauty care products.

As used herein, "transparent" or "visibly clear" is defined as having the property of transmitting light without appreciable scattering so that bodies lying behind are perceivable. One acceptable test method for determining whether a product is clear is to attempt to read a series of words placed immediately behind and contacting one surface of the package, the words being printed in black color, 14 point Times New Roman font, printed on a white sheet of paper. The word and/or letters must be visible and/or readable from the front of the package by an individual using unaided 20/20 eyesight and positioned 12 inches in front of the package in indoor lighting conditions, such as retail outlet lighting conditions.

The term "translucent", as used herein may include "frosted", "glittered", "pearlescence" and the like and is defined herein as the practice of inducing a low level of light scattering into an otherwise "clear" material causing the material to become matted in appearance.

As used herein, "engaged" refers to the means by which the product chamber and the outer jacket (and possibly inner jackets, if present) of the present invention are in contact with each other. Engaged includes direct or indirect contact, permanent, semi-permanent, or temporary contact (such as, for example, being removable).

The terms "semi-permanent" and "permanent" are used herein to describe the nature of how packaging components are engaged with one another. Components that are semi-permanently or permanently engaged with one another are intended to remain with a consumer care product when it is being used. That is, the packaging components are not intended to be removed and discarded prior to using the accompanying consumer care product. Semi-permanent engagement means that the components are designed and configured to permit disengagement, while permanent engagement means that the components are designed and configured to remain connected but could become unconnected through force and/or by destroying or disfiguring the components.

The term "onset of crystallization" as used herein, means the temperature at which a material crystallizes from a liquid solution. All melt points and the onset of crystallization referenced herein, unless otherwise specified, are measured by the well known technique of Differential Scanning calorimetry (DSC). For evaluation, a Perkin-Elmer 7 Series Thermal Analysis System Model DSC7 may be used, manufactured by Perkin-Elmer, Norwalk, Conn.

The term "ambient conditions" as used herein refers to surrounding conditions comprising about one atmosphere of pressure, at about 50% relative humidity, and at about 25° C. All values, amounts and measurements described herein are obtained under ambient conditions unless otherwise specified.

The term "volatile" as used herein refers to those materials which have a measurable vapor pressure at 25° C. Such vapor pressures will typically range from about 0.01 millimeters Mercury (mmHg) to about 6 mmHg, more typically from about 0.02 mmHg to about 1.5 mmHg, and have an average boiling point at one atmosphere (atm) of pressure of less than about 250° C., more typically less than about 235° C. at one atm. Conversely, the term "non-volatile" refers to those materials which are not "volatile" as defined herein.

The term "direct quench" crystallization, as used herein, refers to a cooling process resulting from instantaneously combining together a hot process stream containing a liquid gellant, and a cold process stream, thereby causing substantially the entire amount of the gellant contained in the hot stream being mixed to instantaneously cool to a temperature below the onset of crystallization of the gellant. The term "direct" in this context means that the cold and hot process streams contact one another, and heat and mass transfer occurs, without any layer or other separation between the streams.

All percentages, parts and ratios are by weight of the total composition, unless otherwise specified. All such weights as they pertain to listed ingredients are based on the specific ingredient level and, therefore, do not include solvents, carriers, by-products, filler or other minor ingredients that may be included in commercially available materials, unless otherwise specified.

Figure 2:
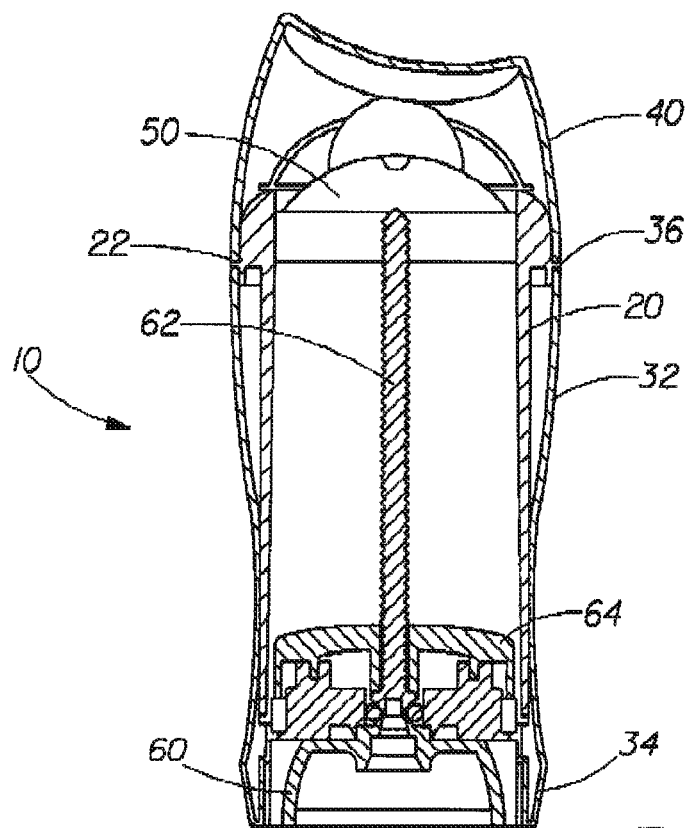
FIG. 2 is a cross sectional view of the exemplary package shown in FIG. 1 taken through line II-II.
Figure 3:
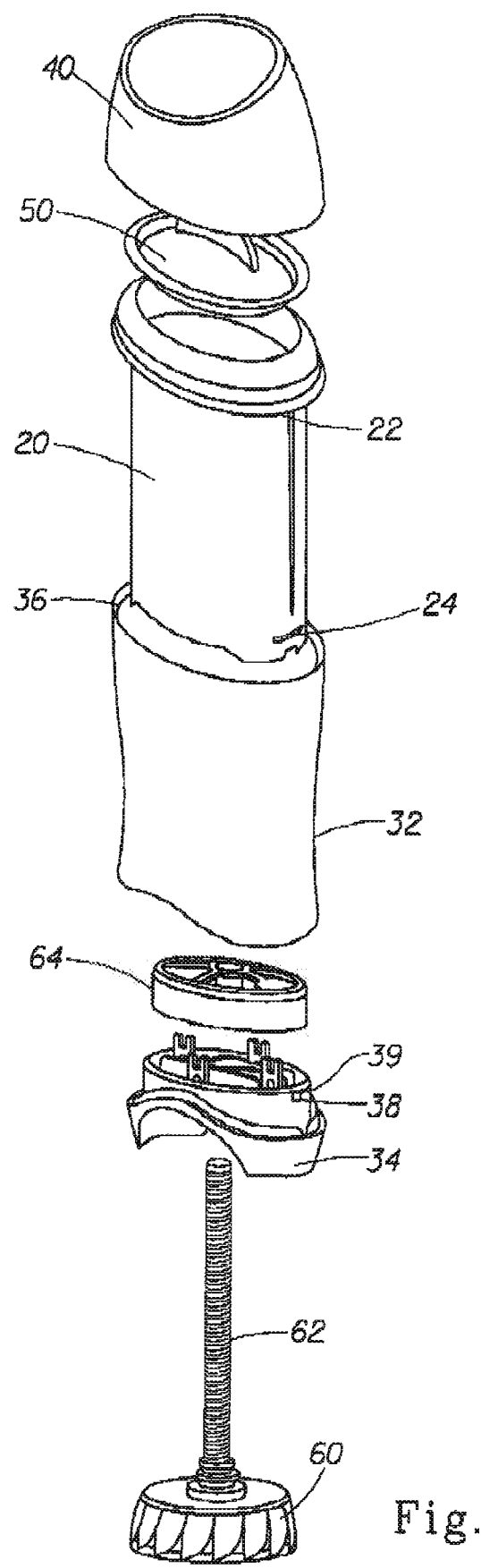
FIG. 3 is en exploded view of the exemplary package shown in FIG. 1 to illustrate at least some of the individual components associated with the exemplary package.

The present invention is directed to self-insulating packaging (e.g., double-walled containers) for holding and dispensing antiperspirant and deodorant compositions, and to processes for filling such packaging. Referring now to the figures, FIGS. 1 to 3 show an exemplary package 10 of the present invention. Package 10 includes a product chamber 20 to which an antiperspirant composition comes into contact, an outer jacket 30 comprising a body (or first) portion 32 and a base (or second) portion 34, and a cap 40. Outer jacket 30 can alternatively be defined by a single portion or more than two portions. A seal 50 is also shown in FIGS. 2 and 3. Seal 50 is intended to protect and maintain the freshness of the antiperspirant composition prior to its purchase and use. A consumer may replace or discard seal 50 after the initial use. The figures further illustrate an exemplary dispensing mechanism that includes an actuator 60 in the form of a dial, a dial shaft 62 that is affixed to actuator 60, and a platform 64 that is axially displaceable via turning actuator 60. A consumer simply rotates actuator 60 causing platform 64 to move upward to urge an antiperspirant solid contained in product chamber 20 out of package 10. It is to be understood that the cap 40, the seal 50, and the dispensing mechanism components can be the same or different from that shown in the figures.

As shown, the body portion 32 of outer jacket 30 is connected to product chamber 20 via tongue and groove features. By way of example only, and as shown in FIGS. 2 and 3, product chamber 20 includes a circumferentially extending groove 22 that is configured to receive a tongue 36 disposed on body portion 32. The respective tongue and groove features can reside on opposite component than that described and illustrated herein. Note that alternative and/or additional connective features or mechanisms may also be employed by packages of the present invention.

The base portion 34 of outer jacket 30 is connected to product chamber 20 via a latch mechanism. The latch mechanism comprises through holes 24 formed in product chamber 20 that are configured to receive projections 38 disposed on base portion 34. As shown, projections 38 have a tapered upper surface 39 to facilitate assembly of base portion 34 and product chamber 20. The through holes 24 and projections 38 create a positive or permanent connection between base portion 34 and product chamber 20, so that the two components are unlikely to become separated during use, even where composition attributes and part tolerances create stress (and strain) during use. Base portion 34 and outer jacket 30 may also include additional connective features, such as, for example, tongue and groove features. Although base portion 34 and outer jacket 30 are illustrated as being connected via a latching mechanism that employs through holes 24, alternative embodiments of the present invention include non-through hole female features, such as, for example, indentations or recesses that are configured to accept male components, such as projections 38. In these alternative embodiments, the female and male connective components may include elements, such as, for example, barbs, angles, steps, and the like, that provide a positive or permanent connection.

In one preferred embodiment, and as illustrated in FIGS. 1 and 2, body portion 32 and base portion 34 are not connected to each other. That is, each of the outer jacket 30 components are connected to product chamber 20, but are themselves unconnected. The components may alternatively be connected to one another.

The material used for the product chamber and outer jacket of the package includes rigid and semi-rigid materials. For example, rigid and semi-rigid materials of the present invention may include, but are not limited to, metals, including but not limited to, aluminum, magnesium alloy, steel; glass; paperboard, including but not limited to, laminates and cardboards; and polymeric materials such as polypropylene (PP), polyethylene (PE), polystyrene (PS), polyethylene-terephtalate (PET), styrene-acrylonitrile copolymer (SAN), polyethylene-terephthalate copolymers, polycarbonate (PC), polyamides, acrylonitrile-butadiene-styrene (ABS) and mixtures thereof. Polymeric materials may also include various fillers known to the skilled artisan, such as, for example, mica, interference pigments, wood flour; or materials that are capable of "blooming" to the surface of a molded component. Whether making rigid or semi-rigid parts, the parts of the product chamber and outer jacket may be manufactured by any number of manufacturing methods known in the art including, but not limited to, injection molding.

The product chamber and outer jacket may be manufactured and subsequently assembled. Antiperspirant compositions may be charged into the product chamber before, after or during the assembly of the product chamber and the outer jacket.

Alternatively, the product chamber and outer jacket may be manufactured, such that the manufacturing process itself imparts at least some connectivity between the components. For example, the product chamber and outer jacket may be formed through a multi-shot molding process or an insert molding process. The molding processes may employ the same or different materials to form the different components. For example, a polymeric material that results in a translucent or transparent part upon curing may be used for the outer jacket and a pigmented polymeric material used for the product chamber. Of course, the product chamber may also be translucent or transparent. The skilled artisan would readily appreciate that the individual components themselves may optionally be made from multiple materials and manufactured through known methods, such as, for example, multi-shot molding and insert molding.

As discussed above, the rigidity or flexibility may differ between the product chamber and outer jacket. A multi-shot process may be employed, for example, to form a relatively rigid product chamber and a relatively flexible outer jacket to impart tactile sensorial benefits. Elastomers or elastomer blends, for example, may be used to manufacture a relatively flexible outer jacket.

Marketing aspects, such as, for example, text and graphics may be disposed on or integrated with the inner and/or outer surfaces of the outer jacket and product chamber, or reside between the two components.

It is to be understood that FIGS. 1-3 and the corresponding description above is provided merely as an example of packages contemplated by the present invention. Numerous variations and changes are permitted and included within the scope of the appended claims.

The double-wall feature, and air pockets existing between some regions of the adjacent walls, increases the insulating property of exemplary package 10. Thus, exemplary package 10 tends to create a relatively inefficient heat transfer environment. Antiperspirant compositions having an elevated temperature when being charged into such a package will accordingly take longer to cure/solidify, as it will take longer for the residual heat to transfer away from the composition and surrounding package components. This increased cure time can result in several disadvantages. One disadvantage is undesirable product attributes in the final antiperspirant product. For example, antiperspirant actives and other materials may tend to settle while the composition is curing so that a consumer will get varying levels of wetness protection efficacy across multiple uses from top to bottom of the product. Furthermore, a relatively slow curing rate can create larger gellant crystals and a wide distribution of gellant crystal sizes such that the final product has a varying "feel" on the underarm skin across multiple uses. Another disadvantage is the potential for added costs and complexity to manufacturing lines due to addition of cooling and/or routing equipment necessary to cool the product further before final packing and shipping. The present invention provides manufacturing processes for making and subsequently filling antiperspirant compositions into self-insulting packages to address these disadvantages.

Figure 4:
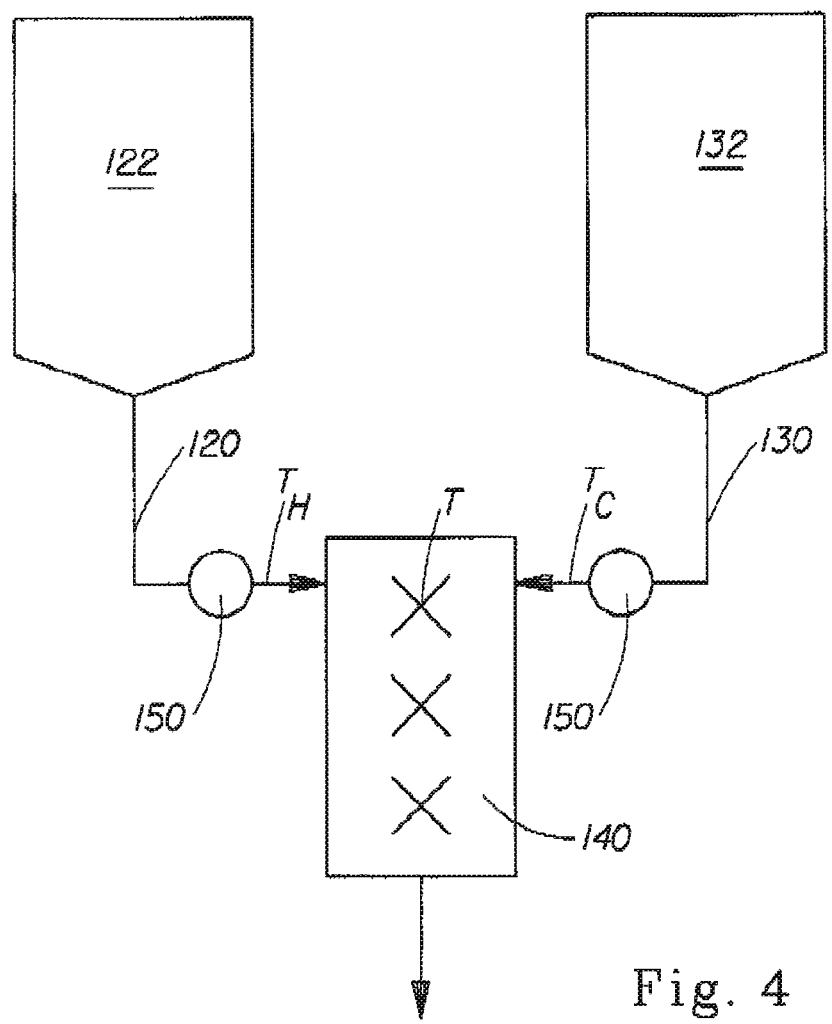
FIG. 4 is a schematic diagram of an exemplary manufacturing process of the present invention.

Referring now to FIG. 4, a schematic of an exemplary process 100 is shown, including a relatively hot process stream 120 and a relatively cold process stream 130 that are brought together in a mixing chamber 140 to form a mixed process stream. Pumps 150 employed to facilitate transfer of the respective streams to mixing chamber 140 are also shown. Mixing chamber 140 may include static and/or dynamic mixing features. The temperature Th of the hot process stream 120 can be from about 1° C. to about 50° C. above the onset of crystallization of a gellant included in the hot process stream. The temperature Tc of cold process stream 130 can be at least 5° C., more specifically at least 20° C., more specifically at least 40° C., and even more specifically at least 60° C., lower than the temperature Th of hot process stream 120. The temperature of the hot process stream, the cold process stream, and the resulting, combined, product stream can be measured by any method known in the art. The temperature of the hot process stream Th and the temperature of the cold process stream Tc can be measured just before the two streams combine; and the temperature of the product (or mixed process) stream T can be measured right after the hot and cold streams have been combined, as schematically shown in FIG. 4.

The ratio, by weight, of the hot process stream to the cold process stream at the point of combining the streams together can be from about 1:9 to about 4:1. Put another way, the hot process stream may comprise from about 10 percent to about 80 percent of the final composition. When making a soft solid antiperspirant/deodorant, one preferred ratio of cold process stream to hot process stream is 3:1; and when making a solid stick antiperspirant/deodorant, one preferred ratio of cold process stream to hot process stream is 1.5:1. Other ratios than those explicitly recited in this paragraph may also be suitable for chosen compositions and product forms.

The step of forming a hot process stream involves mixing a solvent and a gellant so that the melted gellant is dissolved or suspended in the solvent. The hot process stream has a first temperature that may range from 1° C. to 50° C. above the onset of crystallization of the hot process stream. The gellant and solvent may be combined and mixed using a static mixer or alternately may be combined and mixed in a hot process tank 122 (see FIG. 4) using conventional process equipment known to those skilled in the art.

The solvent can be any material that is liquid at the holding temperature of the hot process stream and that can essentially completely dissolve or suspend the gellant. The solvent can be selected from the group consisting of cyclic, linear and branched chain silicones. Suitable solvents may comprise, but are not limited to, non-volatile paraffinic hydrocarbon fluids such as those described in U.S. Pat. No. 4,985,238 and anhydrous liquid carriers such as those described in U.S. Pat. No. 6,171,601 or in U.S. Pat. No. 6,258,346 and emollients such as those described in U.S. Pat. No. 5,972,319. Solvents comprising cyclomethicone are believed to be beneficial.

The gellant can be any material which can crystallize from the hot process stream and remain solid at room temperature. Suitable gellants can include, but are not limited to, those described in U.S. Pat. No. 6,258,346 and those described as nucleating agents or gellants in U.S. Pat. No. 6,171,601, or those waxes and wax-like materials described in U.S. Pat. No. 4,985,238 and may be selected from, but not limited to, the group consisting of stearyl alcohol and other fatty alcohols; hydrogenated castor oil; paraffin wax; beeswax; carnauba; candelilla; spermeceti wax; ozokerite; ceresin; baysberry; synthetic waxes, such as Fisher-Tropsch waxes and microcrystalline wax; polyethylenes with molecular weight of about 200 to about 1000 daltons; solid triglycerides; and any mixtures thereof.

The step of forming a cold process stream involves mixing an antiperspirant or deodorant or cosmetic active, as described herein, and a solvent and optionally a heat sensitive component in a cold process tank 132 (see FIG. 4). The cold process stream may include a liquid emollient or solvent. Suitable liquid emollients or solvents may be selected from the group consisting of mineral oil; PPG-14 butyl ether; isopropyl myristate; petrolatum; butyl stearate; cetyl octanoate; butyl myristate; myristyl myristate; C12-15 alkylbenzoate (e.g., Finsolv™); octyldodecanol; isostearyl isostearate; octododecyl benzoate; isostearyl lactate; isostearyl palmitate; isobutyl stearate; dimethicone and any mixtures thereof. The liquid emollient for the cold process stream may comprise, but is not limited to, the aforementioned solvents for use in the hot process stream. The liquid emollient or solvent can be selected from the group consisting of cyclomethicone, mineral oil; PPG-14 butyl ether; isopropyl myristate; petrolatum; butyl stearate; cetyl octanoate; butyl myristate; myristyl myristate; C12-15 alkylbenzoate (e.g., Finsolv™); octyldodecanol; isostearyl isostearate; octododecyl benzoate; isostearyl lactate; isostearyl palmitate; isobutyl stearate; dimethicone and any mixtures thereof.

The cold process stream may also optionally comprise any heat sensitive component that could chemically degrade or deteriorate or react with components of the cosmetic or antiperspirant composition at elevated temperatures or corrode metal process equipment at elevated storage temperatures. Suitable antiperspirant actives and suitable cosmetic actives may include, but are not limited to those described below. Preferably the cold process stream contains the antiperspirant active.

The antiperspirant active for use in the antiperspirant and deodorant embodiments of the present invention can include any aluminum-containing material having antiperspirant activity, which can be used alone or in combination with other antiperspirant active materials such as zirconium-containing actives. The antiperspirant actives suitable for use herein include astringent metallic salts, especially inorganic and organic salts of aluminum, zirconium and zinc, as well as mixtures thereof. Particularly beneficial are aluminum-containing and/or aluminum/zirconium-containing salts or materials, such as aluminum halides, aluminum chlorohydrate, aluminum hydroxyhalides, zirconyl oxyhalides, zirconyl hydroxyhalides, and mixtures thereof.

Beneficial are aluminum salts for use in the antiperspirant and deodorant embodiments of the present invention include those that conform to the formula:

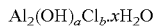

$Al_2(OH)_aCl_b \cdot xH_2O$ wherein a is from about 2 to about 5; the sum of a and b is about 6; x is from about 1 to about 6; and wherein a, b, and x may have non-integer values. Aluminum chlorohydroxides referred to as "5/6 basic chlorohydroxide", wherein a=5, and "2/3 basic chlorohydroxide", wherein a=4, are believed to be beneficial. Processes for preparing aluminum salts are disclosed in U.S. Pat. No. 3,887,692, Gilman, issued Jun. 3, 1975; U.S. Pat. No. 3,904,741, Jones et al., issued Sep. 9, 1975; U.S. Pat. No. 4,359,456, Gosling et al., issued Nov. 16, 1982; and British Patent Specification 2,048,229, Fitzgerald et al., published Dec. 10, 1980, all of which are incorporated herein by reference. Mixtures of aluminum salts are described in British Patent Specification 1,347,950, Shin et al., published Feb. 27, 1974, which description is also incorporated herein by reference.

Beneficial zirconium salts for use in the antiperspirant and deodorant embodiments of the present invention include those which conform to the formula:

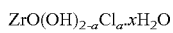

$ZrO(OH)_{2-a}Cl_a \cdot xH_2O$ wherein a is from about 1.5 to about 1.87; x is from about 1 to about 7; and wherein a and x may both have non-integer values. These zirconium salts are described in Belgian Patent 825,146, Schmitz, issued Aug. 4, 1975, which description is incorporated herein by reference. Particularly beneficial zirconium salts are those complexes which additionally contain aluminum and glycine, commonly known as ZAG complexes. These ZAG complexes contain aluminum chlorohydroxide and zirconyl hydroxy chloride conforming to the above-described formulas. Such ZAG complexes are described in U.S. Pat. No. 3,679,068, Luedders et al., issued Feb. 12, 1974; Great Britain Patent Application 2,144,992, Callaghan et al., published Mar. 20, 1985; and U.S. Pat. No. 4,120,948, Shelton, issued Oct. 17, 1978, all of which are incorporated herein by reference.

Antiperspirant actives suitable for use in the compositions include aluminum chlorohydrate, aluminum dichlorohydrate, aluminum sesquichlorohydrate, aluminum chlorohydrex propylene glycol complex, aluminum dichlorohydrex propylene glycol complex, aluminum sesquichlorohydrex propylene glycol complex, aluminum chlorohydrex polyethylene glycol complex, aluminum dichlorohydrex polyethylene glycol complex, aluminum sesquichlorohydrex polyethylene glycol complex, aluminum zirconium trichlorohydrate, aluminum zirconium tetrachlorohydrate, aluminum zirconium pentatchlorohydrate, aluminum zirconium octachlorohydrate, aluminum zirconium trichlorohydrex glycine complex, aluminum zirconium tetrachlorohydrex glycine complex, aluminum zirconium pentachlorohydrex glycine complex, aluminum zirconium octachlorohydrex glycine complex, aluminum chloride, aluminum sulfate buffered, and combinations thereof. Further suitable antiperspirant actives are described in U.S. Pat. No. 6,663,854 or in US 20040009133, the descriptions of which are incorporated herein by reference.

The antiperspirant active concentration can range from about 0.1% to about 30%, more specifically from about 5% to about 30%, by weight of the composition. These weight percentages are calculated on an anhydrous metal salt basis exclusive of water and any complexing agents such as glycine, glycine salts, or other complexing agents. The antiperspirant active can be solubilized or solid, but is preferably in the form of a dispersed solid particulate. The dispersed particulates most typically have average particle size or diameter of less than about 100 micron, more typically from about 1 micron to about 40 micron. The particle size can be measured by using light microscopy methods or any light-scattering technique known in the art.

The antiperspirant and deodorant compositions of the present invention can also or alternatively be formulated with an underarm active in the form of an antimicrobial deodorant material in addition to or in place of the antiperspirant active. Deodorant active concentrations in the compositions can range from about 0.1% to about 30%, specifically from about 0.1% to about 10%, even more specifically from about 0.1% to about 3%, by weight of the composition. These deodorant actives include any known or otherwise safe and effective antimicrobial deodorant active suitable for topical application to human skin, and which is effective in preventing or eliminating malodor associated with perspiration.

Non-limiting examples of antimicrobial deodorant actives for use in the antiperspirant and deodorant compositions of the present invention include cetyl-trimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmethyl sarcosine, lauroyl sarcosine, N-myristoyl glycine, potassium N-lauryl sarcosine, trimethyl ammonium chloride, sodium aluminum chlorohydroxy lactate, triethyl citrate, tricetylmethyl ammonium chloride, 2,4,4'-trichloro-2'-hydroxy diphenyl ether (triclosan), 3,4,4'-trichlorocarbanilide(triclocarban), diaminoalkyl amides such as L-lysine hexadecyl amide, heavy metal salts of citrate, salicylate, and piroctose, especially zinc salts, and acids thereof, heavy metal salts of pyrithione, especially zinc pyrithione, zinc phenolsulfate, farnesol, and combinations thereof. Triclosan, triclocarban, and combinations thereof are believed to be beneficial. Other deodorant actives suitable for use herein are described in U.S. Pat. No. 6,013,248 (Luebbe et al.), which descriptions are incorporated herein by reference.

Compositions of the present invention may also comprise from about 0.01% to about 60% by weight of a cosmetic active. Suitable actives include any known or otherwise effective cosmetic active that is compatible with the essential ingredients of the cosmetic sticks of the present invention, or which do not otherwise unduly impair the product performance thereof.

Cosmetic actives suitable for use in the compositions of the present invention include moisturizers, emollients, perfumes or fragrances, skin conditioners, antiperspirants, anti-oxidants, vitamins, anti-wrinkle products, surfactants, pharmaceuticals, deodorants, pigments or colorants, sunscreens or other photo protectants, and any other material intended or otherwise suitable for topical application to the skin.

Non-limiting examples of cosmetic actives suitable for use herein are described in U.S. Pat. No. 6,001,377 (Sallogueira, Jr. et al.), U.S. Pat. No. 6,024,942 (Tanner et al.), U.S. Pat. No. 6,013,271 (Doughty et al.), and U.S. Pat. No. 6,013,270 (Hargraves et al.), U.S. Pat. No. 6,013,248 (Luebbe et al.) U.S. Pat. No. 5,976,514 (Guskey et al.), which descriptions are hereby incorporated herein by reference.

Specific examples of cosmetic actives suitable for use herein include antiperspirant and deodorant actives as described herein, perfumes and fragrances, antimicrobials (antibacterial, antifungal), steroidal anti-inflammatory materials (e.g., hydrocortisone), non-steroidal anti-inflammatory materials, vitamins and derivatives thereof (e.g., thiamin, riboflavin, niacin, pyridoxine, vitamin A, vitamin D, vitamin E, vitamin K), hydroxy and alpha-hydroxy acids (e.g., salicylic acid, citric acid), moisturizers (e.g., silicone and non-silicone), and the like.

Referring again to FIG. 4, when the hot and cold process streams are combined together, a substantial amount of the hot process stream can be cooled to a temperature of at least 1° C., more specifically at least 3° C., and even more specifically at least 5° C., below the onset of crystallization of a resulting, mixed, product stream. Temperature T of the mixed process stream is preferably more than 15° C. lower than Th, and more preferably more than 20° C. lower than Th, and even more preferably more than 30° C. lower than Th, within a short distance of the point of combining the hot process stream and the cold process stream within mixing chamber 140 so as to effectuate rapid quenching and uniform crystal nucleation.

Given a certain proportion of the hot and cold process streams within a targeted range, the cold process stream preferably has a temperature sufficient to cause substantially the entire amount of the hot process stream being mixed to cool to a temperature that is at least 1° C. lower than the onset of crystallization of the gellant, when the hot and cold process streams are combined within the mixing chamber 140. More specifically, the temperature of the mixed process stream within the mixing chamber 140 is at least 3° C., more specifically at least 5° C., lower that the onset of crystallization of the gellant. The cold process stream can be held at ambient temperature. In a preferred embodiment, the two process streams 120, 130 are combined and mixed within a mixing chamber 140 to effect a quench cooling rate of the "hot" stream of at least 30° C. per second, more specifically at least 50° C. per second, and more specifically at least 100° C. per second.

One of the advantages of the above-described process is that combining the hot and cold process streams together in a manner as to effect direct contact quench cooling allows for greater nucleation which produces very small, uniform crystals—less than about 10 microns in preferred embodiments—in the resulting product. As one skilled in the art will recognize, the crystal size can be measured by using cross-polarized light microscopy methods.

Figure 5:
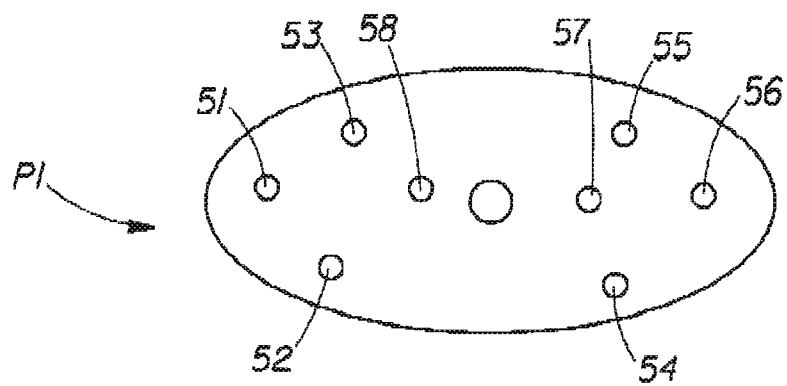
FIG. 5 is a schematic showing an exemplary test location pattern for use with the penetration test method described herein.

Improved product uniformity is another advantage associated with the processes described herein. A penetration test method is one technique for measuring product uniformity, particularly for solid antiperspirant and deodorant compositions. The penetration test is designed to be run on samples that are conditioned at ambient conditions for 24 hours. Samples are prepared by advancing a solid antiperspirant to about ¼ inch above the rim of its container. This advanced portion is then severed to expose a relatively clean, flat surface. A standard mechanical force analyzing instrument, such as a Texture Analyzer model TA-XT2i from Texture Technologies Corporation, is used for the penetration measurements. The instrument is equipped with a round, cylindrical probe measuring 0.040 inch in diameter. The probe extends approximately 1 inch below where it attaches to the instrument. For each sample run, the probe is advanced into the prepared surface of the sample at a rate of 5 mm/sec for 2 seconds (total penetration of 1 cm). The resistant force is measured at a rate of 200 data points per second. Multiple readings (at least 8) are taken for each sample. Each reading is no closer than 3 mm from an adjacent wall of the sample container, no closer than 3 mm from a center screw hole (or axis), and no closer than 5 mm from another reading site. A typical pattern P1 is shown in FIG. 5, with reading sites 51-58.

Various metrics can be recorded using the penetration test, including maximum peak force and Hardness Modulus, which is calculated as the maximum slope (force/time) between any four consecutive data points gathered during the first 0.5 sec of the test run in the linear visco-elastic region. Standard deviations of the peak force and Hardness Modulus are calculated across the multiple reading sites (for example across the 8 sites shown in FIG. 5). Five samples are tested and average standard deviations can be used to compare products.

Solid antiperspirant compositions, in accordance with the present invention, preferably exhibit an average standard deviation of less than or equal to about 5 of penetration peak force measurements, and an average standard deviation of less than or equal to about 40 of Hardness Modulus measurements, taken in accordance with the above-described penetration test method. It is to be understood that process embodiments of the present invention may produce compositions having standard deviation values outside of these preferred ranges.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for making a consumer product, the method comprising the steps of:
   (a) providing a container;
   (b) providing a material process stream comprising a gellant and heating the material process stream to a first temperature to substantially completely melt the gellant;
   (c) lowering the material process stream to a second temperature that is lower than the first temperature by at least 10° C., but is still above the onset of crystallization of the gellant;
   (d) after and/or during step (c), adding an antiperspirant and/or deodorant active to the material process stream to form an antiperspirant composition;
   (e) charging a volume of the antiperspirant composition into the container;
   (f) disposing an outer jacket at least partially around the container to define a double-walled container; and
   (g) achieving an antiperspirant composition temperature that is lower than the second temperature by 15° C. within 30 minutes of completing steps (e) and (f).

2. The consumer product of claim 1, wherein the outer jacket is permanently or semi-permanently engaged with the product chamber.

3. The process of claim 1, wherein step (f) is performed after step (e).

4. The process of claim 3, wherein the second temperature is at least about 40° C. below the first temperature.

5. The method of claim 4, wherein the consumer product comprises a uniform crystal size of less than 10 microns.

6. The process of claim 3, wherein the second temperature is at least about 60° C. below the first temperature.

7. The process of claim 3, wherein the hot process material stream comprises from about 10 to about 75 percent, by weight, of the mixed process stream.

8. The consumer product of claim 3, wherein the outer jacket is permanently or semi-permanently engaged with the product chamber.

9. The process of claim 1, wherein performing step (d) accomplishes step (c).

10. A process for making a consumer product, the method comprising the steps of:
    (a) providing a double-walled container comprising a product chamber and an outer jacket that at least partially surrounds the product chamber;
    (b) forming a hot material process stream comprising a solvent and a gellant dissolved therein, the hot process material stream having a first temperature;
    (c) forming a cold process stream comprising an antiperspirant and/or deodorant active and having a second temperature, wherein the second temperature is at least 20° C. below the first temperature;
    (d) combining the hot material process stream and the one cold material process stream together in a mixing chamber to form a mixed process stream; and
    (e) charging a volume of the mixed process stream into the product chamber.

11. The process of claim 1, wherein the consumer product comprises a uniform crystal size of less than 10 microns.

12. The method of claim 11, wherein the consumer product comprises a uniform crystal size of less than 10 microns.

* * * * *